United States Patent [19]

Torode et al.

[11] 4,209,513

[45] Jun. 24, 1980

[54] TABLET FORMULATION

[75] Inventors: Allan J. Torode, Basildon; David Harden, Sidcup; John Spence, Bickley, all of England

[73] Assignee: Burroughs Wellcome Co., Research Triangle Park, N.C.

[21] Appl. No.: 896,297

[22] Filed: Apr. 14, 1978

Related U.S. Application Data

[63] Continuation of Ser. No. 743,690, Nov. 22, 1976, abandoned, which is a continuation of Ser. No. 549,541, Feb. 13, 1975, abandoned.

[30] Foreign Application Priority Data

Feb. 14, 1974 [GB] United Kingdom ............... 6758/74

[51] Int. Cl.$^2$ ............................................. A61K 47/00
[52] U.S. Cl. .................... 424/228; 424/229; 424/251; 424/361; 424/362
[58] Field of Search ......... 424/228, 229, 251, 358–363

[56] References Cited

U.S. PATENT DOCUMENTS

| | | | |
|---|---|---|---|
| 3,034,911 | 5/1962 | McKee et al. .................. | 424/361 X |
| 3,424,842 | 1/1969 | Nurnberg ........................ | 424/94 |
| 3,619,292 | 11/1971 | Brouillard et al. ............. | 424/361 X |
| 3,622,677 | 11/1971 | Short et al. .................... | 424/361 X |
| 3,632,778 | 1/1972 | Sheth et al. .................... | 424/361 X |
| 3,639,169 | 1/1972 | Broeg et al. .................... | 424/361 X |
| 3,679,794 | 7/1972 | Bentholm et al. .............. | 424/361 X |
| 3,725,556 | 4/1973 | Hanssen et al. ................ | 424/361 X |
| 3,852,421 | 12/1974 | Koyanagi et al. .............. | 424/361 X |

FOREIGN PATENT DOCUMENTS

74-6108 9/1974 South Africa.
1346710 2/1974 United Kingdom.

OTHER PUBLICATIONS

Fincher, J. Pharm. Sci. 57(11): 1825–1835, Nov. 1968, "Particle Size of Drugs and its Relationship to Absorption and Activity".

P.D.R. 28th Ed. (1974) Physicians Dest Reference, pp. 658–659, ("Septra" B–W), pp. 1215–1216, ("Bactrim" H. LaRoche).

Mendell Mfg. Chemist, Apr. 1972, "Direct Compression Method of Producing Solid Dosage Forms".

*Primary Examiner*—Shep K. Rose
*Attorney, Agent, or Firm*—Donald Brown

[57] ABSTRACT

A tablet suitable for use in the treatment of microbial infections, which tablet comprises from 80 to 98% (w/w) of a combination of a 2,4-diaminopyrimidine with a sulphonamide and not more than 20% (w/w) of both a granulating and a disintegrating agent, the combination having a particle size less than 40 μm and the disintegrating agent having a swelling capacity greater than 5 ml/g.

9 Claims, No Drawings

TABLET FORMULATION

This is a continuation of application Ser. No. 743,690 filed Nov. 22, 1976 which is a continuation of Ser. No. 549,541 filed Feb. 13, 1975, both now abandoned.

This invention relates to pharmaceutical formulations containing a combination of a 2,4-diaminopyrimidine with a sulphonamide, such formulations being suitable for oral administration.

2,4-Diaminopyrimidines are well known not only as folic and folinic acid antagonists in microorganisms which require these nutrients but also as inhibitors of the enzyme dihydrofolate reductase in *Streptococcus faecalis*. When these compounds are used in combination with sulphonamides, a strong potentiative effect against a broad spectrum of microbes is observed as a consequence of the sequential blockade of the biochemical pathway which leads to the de novo synthesis of coenzymes F. Hence, 2,4-diaminopyrimidines are frequently referred to as sulphonamide potentiators. This potentiation may be demonstrated both *in vitro* and in mice infected with *Staphyloccoccus* or *Proteus* species. Indeed, such is the potentiative effect experienced that considerable success has been achieved in the treatment of microbially-infected animals and human beings.

The most commonly used 2,4-diaminopyrimidine is trimethoprim [2,4-diamino-5-(3,4,5-trimethoxybenzyl)-pyrimidine] which is usually combined with sulphamethoxazole [3-(4-aminobenzenesulphonamido-5-methylisoxazole] in a ratio of 1:5 (trimethoprim: sulphamethoxazole). For example, tablets containing 400 mg of sulphamethoxazole and 80 mg of trimethoprim have been available for some years.

Although the dosage of a combination of a 2,4-diaminoprimidine with a sulphonamide, hereinafter the combination being referred to as the 'active ingredient', depends to some extent on type of infection which is being treated, it is usual to employ a dosage from 100 to 900 mg, for example about 500 mg, which dosage in some cases is given to adult patients two or more times per day. Such amounts of active ingredient are normally administered in the form of a tablet in which the propertion of active ingredient is usually between 60 and 80% (w/w). The remaining proportion of the tablet is normally taken up with conventional excipients such as a disintegrating agent, a granulating or binding agent, a lubricating agent and an inert filler.

At present, the administration of these tablets frequently meets with difficulties owing to their necessarily large size even when the amount of active ingredient is as low as 400 mg and constitutes a proportion of the tablet as high as 80% (w/w). Moreover, these difficulties increase when a large amount of active ingredient, for example greater than 600 mg, is given to an adult patient in a single dose, as is often the case. Thus, it is usually found that a patient is reluctant to swallow such tablets unless their size is reduced.

In addition, it is unfortunate that an increase in the proportion of active ingredient to above 80% (w/w), thereby reducing the overall size of the tablet, has hitherto resulted in poor tablet characteristics, such as a high disintegration or dissolution time, a high friability value or a low hardness value. These characteristics obviously assume the utmost importance primarily for the reason that they may not comply with certain medical standards required by the Health Authorities in many countries. For instance, poor tablet characteristics may well result in abrasion or fragmentation of the tablets during transportation and the patients would not therefore receive the required amount of active ingredient.

It has now been found that a tablet having excellent characteristics can be achieved with a higher proportion of active ingredient present than has hitherto been obtained. In fat, the tablet can be manufactured to contain a proportion as high as 95% (w/w) or even higher. This is made possible by using an active ingredient, i.e. the combination of a 2,4-diaminopyrimidine with a sulphonamide, which has a particle size, as hereinafter defined, of less than 40 $\mu$m. Since a reduction in the proportion of excipients is obviously concomitant with the use of a high proportion of active ingredient, the resulting tablet possesses economic benefits over and above previous tablets.

It has also been found that an increase in the swelling capacity, as hereinafter defined, of a disintegrating agent is associated with a corresponding decrease in the disintegration time of a tablet of the invention. Thus, although the low particle size of the active ingredient provides an improvement in the characteristics of the tablet, the inclusion of a disintegrating agent having a swelling capacity, as hereinafter defined, greater than 5.0 ml/g imparts a further improvement in these characteristics. In particular, surprisingly low disintegration times are now also possible for tablets having a high content, for example 95% (w/w), of active ingredient and, at the same time, a high hardness value, such as 12 kg.

Accordingly, the present invention provides a tablet, which comprises from 80 to 98% (w/w) of a combination of a 2,4-diaminopyrimidine with a sulphonamide, a disintegrating agent and a granulating agent, the total amount of both agents not being more than 20% (w/w) of the formulation, wherein the particle size of the combination is less than 40 $\mu$m and the disintegrating agent has a swelling capacity, as hereinafter defined, greater than 5 ml/g.

In particular, the tablet comprises at least 85% (w/w), preferably 90% (w/w), of active ingredient which is desirably present in a ratio from 1:20 to 20:1, for example 1:5 (2,4-diaminopyrimidine:sulphonamide) and which has a particle size greater than 1 $\mu$m, preferably 2 $\mu$m.

Moreover, a tablet comprising from 1 to 5% (w/w) of a granulating agent and from 1 to 5% (w/w) of a disintegrating agent is further preferred as is a tablet containing a disintegrating agent which has a swelling capacity, as hereinafter defined, greater than 10 ml/g.

A tablet containing from 100 to 900 mg of the active ingredient, for example about 500 mg. constitutes an even further preferred agent of this invention while a tablet which comprises trimethoprim (80 mg) and sulphamethoxazole (400 mg) constitute the most preferred aspect.

The present invention also provides a tablet, said tablet comprising
(a) greater than 80% (w/w) to about 95% of active solid ingredient comprising a sulphonamide and a sulphonamide potentiator,
(b) said active ingredient having a particle size below about 40 $\mu$m to about 1 $\mu$m, and
(c) a disintegrating agent having greater than about a 5 ml/g swelling capacity.

In particular, the tablet contains an amount of active ingredient from 85 to 95% (w/w), preferably from 90 to 95% (w/w).

Moreover, a tablet containing an active ingredient having a particle size from 40 to 2 μm and/or a disintegrating agent having a swelling capacity between 5 ml/g and about 25 ml/g is even further preferred.

As used herein, the particle size of the active ingredient is defined in terms of the "weight median diameter" hereinafter referred to as W.M.D. Thus, each particle is considered as a sphere having a volume identical with the actual particle and the W.M.D. is that 'diameter', wherein 50% (by weight) of these hypothetical spheres have a larger diameter than that figure and 50% (by weight) a smaller diameter tha that figure. The W.M.D. may be determined using a Coulter counter in which the active ingredient, dispersed in an electrolyte comprising an aqueous solution of, for example, sodium chloride saturated with the active ingredient, is passed through a small orifice in a tube on either side of whih is immersed an electrode. The changes in resistance as particles pass through the orifice generate voltage pulses whose amplitudes are proportional to the volumes of the particles. The pulses are amplified, and the numbers counted at different threshold levels. From this data the size distribution of the suspended particles and hence the W.M.D. may be determined.

The particular particle size of the active ingredient which is to be used with the present invention, will depend upon the envisaged content thereof in the resulting tablet. If, for example, 85% (w/w) of active ingredient is required, then the particle size could be, for instance, between 20 and 30 μm. On the other hand, if a 95% (w/w) content of active ingredient is required, it would be advisable to use an even lower particle size, for example, less tha 15 μm, preferably about 10 μm.

The particle size of the active ingredient may readily be reduced by precipitation techniques or by grinding the particles with any apparatus or by any other method known in the art suitable for such a purpose. In particular, the hammer mill, which can be used with either the rigid or the swing-hammer type and is conveniently combined with a fan and a cyclone for collecting the material, is preferred.

As used herein, the swelling capacity of a disintegrating agent is defined as the volume (ml) to which 1 g of a tablet containing 95% (w/w) of the dry, disintegrating agent and 5% (w/w) of polyvinylpyrrollidone (K30) will swell when in contact with an excess of water at a temperature of 21° C. It is determined by granulating the disintegrating agent (2 g) with 10% polyvinlpyrrolidone (K30) (1 ml) and drying the resultant granules at 60° C. Compression of the granules to a hardness value of 12 kg provides tablets having a diameter of 15 mm and a weight of approximately 900 mg. Each tablet is then accurately weighed and placed on the bottom of a 25 ml measuring cylinder. A nylon disc of 8 mm thickness and having two grooves provides a close, but sliding, fit in the measuring cylinder, resting on the top of the tablet. The grooves are disposed opposite each other on the circumference of the disc in a direction at right angles to the plane thereof and allow for a thin hypodermic needle to be inserted between the disc and the glass wall of the measuring cylinder. A 5 g weight is placed on the nylon disc and water injected through one of the grooves into the space surrounding the tablet; the other groove allowing for air to be displaced. When the water level is above the top of the disc, the needle can be removed and water added until it is in excess, e.g. 25 ml. The volume under the disc is then noted at periodic intervals until there is no further increase in absorption. In some cases, disintegrating agents absorb water to form viscous gels, and this slows down the rate of absorption necessitating a longer interval, such as 48 hours, before maximum swelling is achieved.

On completion of swelling, the final volume is read and corrected to the corresponding value for 1 g of the tablet, i.e. the value for the swelling capacity. The whole operation should preferably be performed at an approximately constant room temperature, for example 21° C.

Disintegrating agents which have a swelling capacity greater than 5 ml/g and which therefore may be used in the present invention include calcium carboxy methyl celluloses, such as E.C.G. 505, low viscosity sodium carboxy methyl celluloses, such as Copagel, guar based vegetable gums, such as Supercol U and Supercol G.F., a sodium alginate, such as Alginate YZ, and sodium starch glycolates, such as Primojel. The most preferred disintegrating agents are Supercol U and Primojel.

Granulating agents which may be employed in the present invention include starch in the form of mucilage, starch derivatives, such as starch 'Snow Flake', cellulose derivatives, such as methylcelluose, gelatin and preferably polyvinlpyrrolidine.

2,4-Diaminopyrimidines which may be employed in the present invention include those embraced by formula (I),

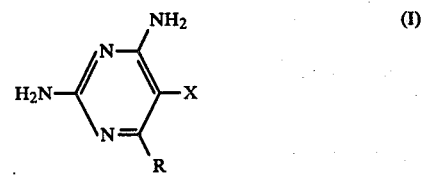

wherein X is an optionally substituted phenyl group when R is an alkyl group having from 1 to 4 carbon atoms or X is an optionally substituted benzyl group when R is a hydrogen atom.

Preferably X is substituted benzyl group of formula (II),

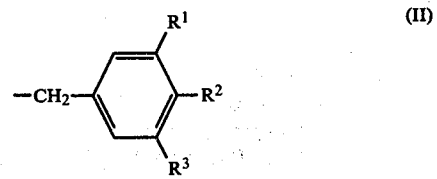

wherein $R^1$, $R^2$ and $R^3$ are the same or different and each can represent an alkyl group having from 1 to 4 carbon atoms, an alkoxy group having from 1 to 4 carbon atoms, a hydrogen atom or $R^1$ and $R^2$ together can represent an alkylenedioxy group having from 1 to 4 carbon atoms, such as methylenedioxy group.

Examples of compounds which fall within formula (I) include the aforementioned trimethoprim, diaveridine{2,4-diamino-5-       -(3,4-dimethoxybenzyl)-pyrimidine},2,4-diamino-5-(3,4,6-trimethoxybenzyl)-pyrimidine, ormetoprim {2,4-diamino-5-(2-methyl-4,5-dimethoxybenzyl)pyrimidine},     2,4-diamino-5-(3,4-dimethoxy-5-bromobenzyl)pyrimidine, and pyrimethamine     {2,4-diamino-5-(4-chlorophenyl)-6-ethylpyrimidine}. The especially preferred compound is trimethoprim.

Sulphonamides which may be employed in the present invention include those embraced by formula (III).

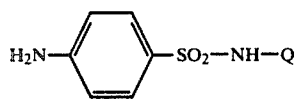

wherein Q is a substituted or unsubstituted pyrimidin-2-yl, pyrimidin-4-yl, a substituted isoxazolyl group, a quinoxalinyl group or an acyl group in which the alkyl group has from 1 to 4 carbon atoms.

Examples of preferred sulphonamides which fall within formula (III) include the aforementioned sulphamethoxazole sulphadimethoxine {6-(4-aminobenzenesulphonamido)-2,4-dimethoxyprimidine}, sulphadiazine {2-(4-aminobenzenesulphonamido)pyrimidine}, sulphadoxine{4-(4-aminobenzenesulphonamido)-5,6-dimethoxypyridimine}, sulphaquinoxalne{2-sulphonamido-quinoxaline}, sulphimidine{2-(4-aminobenzenesulphonamido)-4,6-dimethylpyrimidine)}, sulphafurazole{5-(4-aminobenzenesulphonamido)-3,4-dimethylisoxazole}, and sulphacetamido{N-sulphanilylacetamide}. The especially preferred compound is sulphamethoxazole.

2,4-Diaminopyrimidines and the sulphonamides may be prepared by any one of a number of suitable methods described in the art, for example, 2,4-diamino-5-benzylpyrimidines can conveniently be prepared by the route described and claimed in U.K. Patent Specification No. 1261455 while sulphamethoxazole, for instance, can be prepared by the process disclosed in U.K. Pat. No. 814,276.

It may also be desirable to include a small proportion of a suitable lubricant, such as magnesium stearate, in the tablet so that the tablet is thereby prevented from adhering to the punches and dies of the automatic tabletting equipment. Also dyes and preservatives may be added, if required.

In another aspect of the invention, there is provided a method of preparing a tablet, which comprises the compression on standard machinery of a formulation containing from 80 to 98% (w/w) of a combination of a 2,4-diaminopyrimidine with a sulphonamide, a disintegrating agent and a granulating agent, the total amount of both agents not being more than 20% (w/w) of the formulation, wherein the particles size of the combination is less than 40 μm and the disintegrating agent has a swelling capacity, as hereinbefore defined, greater than 5 ml/g. The active ingredient and disintegrating agent are mixed in a dry state at slow speed, for example around 15 rev/min, in a planetary mixer, followed by wet mixing for up to about 30 minutes with a granulating solution, together with additional solvent, if necessary, for maintaining the consistency of the mass. The material can then be milled and eiter tray-dried or dried in a fluidised bed. The dry material is sifted and a lubricant is added to the granules provided in this manner. Compression of the granules on standard machinery to the specified hardness than gives tablets of the required size and shape.

As used herein, the term (w/w) is used to denote the ratio of the weight of specified excipient or active ingredient to the total weight of the tablet.

It should be noted that the advantageous characteristics of a tablet made in accordance with the present invention are primarily due to the interactions that exist between the disintegrating agent and each at one of the 2,4-diaminopyrimidine, the sulphonamide and the graunlating agent.

The disintegration time may be determined by the method described in the British Pharmacopoeia 1968 which involves the rapid movement of the tablet in water under standardised conditions, until there are no fragments remaining above a supporting wire guage (vide pages 1366 to 1367).

The British Pharmacopoeia 1968 also states that the disintegration time for any tablet must not exceed 15 minutes but desirably this time should be less than 10 minutes, especially below 5 minutes, for safety reasons in view of inevitable variations from tablet to tablet. In addition to this essential requirement it is generally recommended that the moisture content of the granule from which the tablet is produced should be below 2%.

The "hardness" of a tablet is the amount of force required to shatter it or is more correctly the crushing strength, and although this may be measured accurately according to various standards, the Monsanto method is convenient and suitable for testing the tablet produced in accordance with the present invention. Basically the method involves the use of a Monsanto Tablet Hardness Tester, which is a spring-loaded device capable of exerting radial pressure on an edge of the tablet, the shattering force being read from a scale on the sleeve of the device.

The friability of a tablet is a measure of the loss of weight suffered by a tablet from abrasion or shock and may be tested by a "Roche" Friabilator in which a weighed sample of tablets, such as 6 g, is subjected in the apparatus for a length of time, such as 4 minutes, to abrasion caused by a tumbling action, comparable to tablets rubbing one another or being shaken against the walls of their container in general use, and to a shock resulting from a free-fall of six-inches, such as might be encountered during various steps in packaging, handling and transport.

The dissolution time of a tablet may, for instance, be determined according to the U.S.P. XVIII by using an apparatus comprising a cylindrical basket of 1680 μm stainless steel mesh, a covered 1000 ml glass vessel, a constant-temperature water bath, and a variable-speed motor. The dissolution medium, which may be for example 0.6% hydrochloric acid, pH 1.2, is poured into the vessel which has been previously immersed in the constant-temperature bath and the medium is allowed to come to a temperature of 37° C. A tablet is placed in the basket and the apparatus assembled such that the basket is fully immersed in the medium. The basket is rotated at, for example, 120 rev/min. and samples are withdrawn at intervals with a syringe and assayed, for instance, by U.V. absorbance.

Further advantages of the present invention will now become apparent from the following description of embodiments of the invention, which embodiments do not limit this invention in any way.

EXAMPLE 1

The swelling capacity of a variety of disintegrating agents was determined according to the method hereinbefore described at a temperature of 21° C. Each disintegrant tested was then included in the formulation:

|  | weight/(g) |
| --- | --- |
| Sulphamethoxazole | 800 |
| Trimethoprim | 160 |
| Disintegrant | 19 |
| P.V.P. K30 | 20.8 |
| Dioctyl Sodium Sulphosuccinate | 0.8 |
| Magnesium Stearate | 10.0 |

The sulphamethoxazole and trimethoprim, the mixture of which had a particle size of 11.6 μm, together with the disintegrant were dry mixed in a Morton mixer prior to the addition of a solution (260 ml) containing P.V.P. K30 and dioctyl sodium sulphosuccinate in equal parts of alcohol and water. A further addition of a solution (200 ml) containing only equal parts of alcohol and water was added before the wet-mass was passed through a 1000 μm screen. The resulting granules were dried in a fluid bed drier for 20 minutes at 70° C. prior to sifting through a 1000 μm screen.

Magnesium stearate, previously sifted through a 125 μm screen was added to the granules and the resulting mixture compressed on a Manesty D3 rotary compression machine to provide tablets having a hardness value of 12.0 kg (Monsanto).

The characteristics, in particular the disintegration time, were then examined for each tablet formulation.

| DISINTEGRATING AGENT | SWELLING CAPACITY (ml/g) | DISINTEGRATION TIME/min-hz,1/32 |
| --- | --- | --- |
| Supercol U | 23.1 | 1.08 |
| Primojel | 14.8 | 1.42 |
| Alginate YZ | 10.2 | 2.17 |
| Copagel | 5.2 | 3.17 |
| Supercol G.F. | 7.4 | 3.17 |
| E.C.G. 505 | 6.0 | 7.67 |
| Cepo cellulose | 4.8 | >15 |
| Alginic acid | 4.6 | >15 |
| Avicel PH 101 | 3.4 | >15 |
| Veegum regular | 2.3 | >15 |
| Crodamix U.35 | 1.6 | >15 |
| Maize Starch | 1.3 | >15 |

These results establish that the use of a disintegrating agent having a swelling capacity greater than 5 ml in a formulation provides a tablet with superior characteristics, particularly with regard to its disintegration time.

EXAMPLE 2

Sulphamethoxazole (800 g) and trimethoprim (160 g) were mixed and then passed through an Apex comminuting mill fitted with a B. 1762 screen. The mill was run at medium speed with the cutter blades forward to provide an active ingredient having a particle size of 10 μm. The resulting mixture of sulphamethoxazole and trimethoprim was dry mixed with Primojel (20 g) in a Morton mixer.

Gelatin (20 g) was dissolved in water (100 ml) and the solution made up to 200 ml with alcohol. The resulting solution was added to the dry mixture in order to achieve granulation thereof. The resulting wet-mass was sifted through a 1000 μm screen and dried in a fluid bed drier at 60° C. for 20 minutes. The dried granules which had a moisture content of 0.4% were further sifted through a 1000 μm screen.

Magnesium stearate (10 g), previously sifted through a 125 μm screen, was added to the granules and the resulting mixture compressed on a Manesty D3 rotary compression machine to provide tablets having a hardness value of 12.0 kg (Monsanto), a disintegration time of 45 sec. and a friability value of less than 0.2%.

The time for 50% of the tablet to dissolve in 0.6% HCl (pH 1.2), hereinafter referred to as $T_{50}$, and the time for 80% of the tablet to dissolve in 0.6% HCl (pH 1.2), hereinafter referred to as $T_{80}$, were 7 min. and 20 min. respectively.

Each of the tablets had a thickness of 5.5 mm, a diameter of 11 mm, a weight of 505 mg and contained 400 mg of sulphamethoxazole and 80 mg of trimethoprim.

EXAMPLE 3

Sulphamethoxazole (4000 g) and trimethoprim (800 g), the mixture of which had a particle size of 11.6 μm, were dry mixed with Primojel (95 g) in a Beken mixer for 10 minutes. Gelatin (100 g) was dissolved in water (500 ml) and the solution made up to 1000 ml with alcohol. The resulting solution was added to the dry mixture together with solution (250 ml) containing only equal parts of alcohol and water, and mixed for 20 minutes. The resulting wet mass was then passed through an Apex Comminuting Mill fitted with an A9(⅜inch) screen and the granules dried on trays overnight at 50° C. The granules which had a moisture content of 0.47% were further passed through a 1000 μm sieve.

Magnesium stearate (50 g), previously sifted through a 125 μm screen, was added to the granules and the resulting mixture compressed on a Manesty D3 rotary compression machine to provide tablets having a hardness value of 12.0 kg (Monsanto), a disintegration time of 46 seconds and a friability value of less than 0.2%.

The $T_{50}$ and $T_{80}$ values were respectively 4 and 11 mins and each of the tablets had a thickness of 5.56 mm, a diameter of 11 mm, a weight of 505 mg and contained 400 mg of sulphamethoxazole and 80 mg of trimethoprim.

EXAMPLE 4

Sulphamethoxazole (4000 g) and trimethoprim (800 g), the mixture of which had a particle size of 11.6 μm, were dry mixed with Primojel (95 g) in a Beken mixer for 10 minutes. A solution (1300 ml) of P.V.P. K30 (104 g) and dioctyl sodium sulphosuccinate (4 g) in equal parts of alcohol and water was added to the dry mixture together with a further solution (100 ml) containing only equal parts of alcohol and water. The wet-mass was mixed for 10 minutes and then passed through an Apex comminuting Mill fitted with an A9 screen. The resultant granules were dried on trays overnight at 50° C. The dried granules which had a moisture content of 0.70% were then passed through a 1000 μm sieve.

Magnesium stearate (50 g), previously sifted through a 125 μm screen, was added to the granules and the mixture compressed on a Manesty D3 compression machine to provide tablets having a hardness value of 12.4 kg, a disintegration time of 1 min 31 sec and a friability value of less then 0.2%.

The $T_{50}$ and $T_{80}$ values were respectively 7 and 29 mins and each of the tablets had a thickness of 5.33 mm, a diameter of 11 mm, a weight of 508.8 mg and contained 400 mg of sulphamothoxaxole and 80 mg of trimethoprim.

In addition when the mixture was compressed to maximum hardness (>20 kg) the disintegration time was 9 min.

EXAMPLE 5

The procedure of Example 4 was repeated except Primojel was replaced with Supercol U.

Compression of the mixture provided tablets having a hardness value of 12.5 kg, a disintegration time of 1 min 45 sec and a friability value of <0.2%.

The $T_{50}$ and $T_{80}$ values were respectively 8 and 31 min and each of the tablets had a thickness of 5.42 mm, a diameter of 11 mm, a weight of 503.8 mg and contained 400 mg of sulphamethoxazole and 80 mg of trimethoprim.

In addition when the mixture was compressed to maximum hardness (>20kg) the disintegration time was 9 min.

EXAMPLE 6

The procedure of Example 4 was repeated except Primojel was replaced with Alginate YZ.

Compression of the mixture provided tablets having a hardness value of 12 kg, a disintegration time of 1 min 53 sec and a friability value of less than 0.2%.

The $T_{50}$ and $T_{80}$ values were respectively 9 and 31 min and each of the tablets had a thickness of 5.40 mm, a diameter of 11 mm, a weight of 504.0 mg and contained 400 mg of sulphamethoxazole and 80 mg of trimethoprim.

In addition when the mixture was compressed to maximum hardness (>20 kg) the disintegration time was 5 min 25 sec.

EXAMPLE 7

Sulphamethoxazole (400 g) and trimethoprim (80 g), the mixture of which had a particle size of 11.8 μm, and Primojel (24 g) were mixed in the dry state for 10 minutes in a Z-blade mixer. A solution containing gelatin (16 g), dioctyl sodium sulphosuccinate (1 g), alcohol (57 g) and purified water (80 g) was prepared. The solution was wet-mixed with the powders for 10 minutes using a slow speed. The wet mass was passed through a 1000 μm screen. The granules obtained were dried in a fluidised bed at 60° C. for 30 minutes to a moisture content of 0.86%.

The dried granules were sifted through a 1000 μm screen and magnesium stearate (4.8 g), sifted 125 μm, was blended with the granules and the resulting mixture compressed on a Manesty D3 Rotary machine to provide tablets having a hardness value of 14.5 kg (Monsanto), a disintegration time of 58 seconds and a friability value of 0.46%.

The $T_{50}$ and $T_{80}$ values were respectively 2 min and 3 min and each of the tablets had a thickness of 5.8 mm, a diameter of 11 mm, a weight of 526 mg and contained 400 mg of sulfamethoxazole and 80 mg of trimethoprim.

EXAMPLE 8

Sulphamethoxazole (400 g) and trimethoprim (80 g), the mixture of which had a particle size of 11.8 μm, Primojel (80 g) and lactose (30 g) were granulated as in Example 7. The granules were dried to a moisture content of 1.43%.

After sifting through a 1000 μm screen, magnesium stearate (4.8 g), previously sifted through a 125 μm screen, was blended with the granules and the resulting mixture was compressed on a Manesty D3 Rotary machine to provide tablets having a hardness value of 14.8 kg (Monsanto), a disintegration time of 1 min 53 sec and a friability value of 0.34%.

The $T_{50}$ and $T_{80}$ values were respectively 2 min and 4 min and each of the tablets had a thickness of 6.3 mm, a diameter of 11 mm, a weight of 572 mg and contained 400 mg of sulphametoxazole and 80 mg of trimethoprim.

EXAMPLE 9

Sulphamethoxazole (80 g) and trimethoprim (400 g), the mixture of which had a particle size of 28.4 μm, pregelled starch (96 g) and Primojel (16 g) were mixed in the dry state for 10 minutes in a Z-blade mixer. Purified water (200 g) was wet mixed with the powders for 10 minutes. The wet mass was passed through a 1000 μm screen and then the granules were dried to a moisture content of 1.25%.

Magnesium stearate (4.8 g), previously sifted through a 125 μm screen, was added to the dried granules and the resulting mixture was compressed on a Manesty D3 Rotary machine to provide tablets having a hardness value of 9.8 kg (Monsanto), a disintegration time of 6 min 10 sec and a friability of 0.30%. The $T_{50}$ and $T_{80}$ values were respectively 5 and 11 min and each tablet had a thickness of 6.69 mm, a diameter of 11 mm, a weight of 597 mg and contained 80 mg of sulphamethoxazole and 400 mg of trimethoprim.

EXAMPLE 10

Sulphamethoxazole (400 g) and trimethoprim (400 g), the mixture of which had a particle size of 11 μm, and Primojel (32 g) were mixed in the dry state for 10 minutes. A solution containing polyethylene glycol 5000 (28 g) and purified water (122 g) was prepared. The solution was wet mixed with the powders for 10 minutes. The granules were prepared as in Example 7. The granules were dried to a moisture content of 1.1%.

Magnesium stearate (4.8 g), previously sifted through a 125 μm screen, was added to the dried granules and the resulting mixture was compressed on a Manesty D3 Rotary machine to provide tablets having a hardness value of 14.4 kg (Monsanto), a disintegration time of 7 min 15 sec and a friability of 0.33%. The $T_{50}$ and $T_{80}$ values were respectively 14 min and 35 min and each tablet had a thickness of 5.50 mm, a diameter of 11 mm, a weight of 545 mg and contained 440 mg of sulphamethoxazole and 40 mg of trimethoprim.

EXAMPLE 11

Sulphamethoxazole (400 g) and trimethoprim (80 g), the mixture of which had a particle size of 11.8 μm, and Alginate YZ (96 g) were mixed in the dry state for 10 minutes. A solution containing polyvinylpyrrolidone K.30 (16 g), alcohol (80 g) and purified water (100 g) was prepared and then wet mixed with the powders for 10 minutes using slow speed. The granules were prepared as in Example 1 and dried to a moisture content of 1.0%.

The dried granules were sifted through a 1000 μm screen and magnesium stearate (4.8 g), sifted 125 μm, was blended with the granules and the resulting mixture compressed on a Manesty BB3 Rotary machine to provide tablets having a hardness value of 12.7 kg (Monsanto), a disintegration time of 6 min 25 sec and a friability value of 0.2%.

The $T_{80}$ value was 5 min and each of the tablets had a thickness of 6.7 mm, a diameter of 11 mm, a weight of 597 mg and contained 400 mg of sulphamethoxazole and 80 mg of trimethoprim.

What we claim is:

1. In a tablet comprising a combination of trimethoprim and sulphamethoxazole, the combination having a particle size of from 1 to 40 μm, together with a granulating agent and a disintegrating agent, the improvement wherein the tablet comprises from 90 to 98 percent (w/w) of the combination of trimethoprim with sulphamethoxazole, from 1 to 5 percent of the granulating agent and from 1 to 5 percent of the disintegrating agent, said disintegrating agent having a swelling capacity of from 5 to about 25 ml/g and the tablet having a hardness of about 9.8 to 20 kg and a disintegration time of less than 9 minutes.

2. In the tablet according to claim 1 in which the disintegrant is selected from the class consisting of calcium carboxymethyl cellulose, low viscosity sodium carboxymethyl cellulose, guar based vegetable gum, sodium alginate and sodium starch glycolate.

3. In the tablet according to claim 2 in which the granulating agent is selected from the class consisting of starch in the form of mucilage, starch in the form of 'Snow Flake', methylcellulose, gelatin and polyvinylpyrrolidine.

4. In the tablet according to claim 1 in which the ratio of trimethoprim to sulphamethoxazole is 1:5.

5. In the tablet according to claim 4 in which the disintegrant is sodium starch glycolate.

6. In the tablet according to claim 3 in which the disintegrant is sodium starch glycolate.

7. In the tablet according to claim 6 in which the ratio of trimethoprim to sulphamethoxazole is 1:5.

8. A tablet according to claim 1 wherein the tablet has a hardness of about 9.8 to about 14.8 kg.

9. A tablet according to claim 4 wherein the disintegration time is from 45 seconds to about 5 minutes.